(12) United States Patent
Dreibholz et al.

(10) Patent No.: US 9,335,333 B2
(45) Date of Patent: May 10, 2016

(54) TEST TAPE CASSETTE AND ANALYTICAL TEST TAPE THEREFOR

(71) Applicant: Roche Diabetes Care, Inc.

(72) Inventors: Joerg Dreibholz, Altrip (DE); Christian Freitag, Weinolsheim (DE); Thomas Jaeck, Heddesheim (DE); Ingrid Keth, Worms (DE); Rudolf Pachl, Ellerstadt (DE); Elke Schmidtchen, Mannheim (DE); Wolfgang Schwoebel, Mannheim (DE); Peter Seelig, Frankfurt am Main (DE)

(73) Assignee: Roche Diabetes Care, Inc., Indianapolis ( * ) Notice: Subject to any disclaimer, the term of this patent is extended or adjusted under 35 U.S.C. 154(b) by 25 days.

(21) Appl. No.: 14/200,805

(22) Filed: Mar. 7, 2014

(65) Prior Publication Data

US 2014/0186213 A1    Jul. 3, 2014

Related U.S. Application Data

(63) Continuation of application No. PCT/EP2012/068145, filed on Sep. 14, 2012.

(30) Foreign Application Priority Data

Sep. 16, 2011    (EP) .................................... 11181718

(51) Int. Cl.
*G01N 35/00* (2006.01)
*G01N 21/84* (2006.01)
*G01N 33/487* (2006.01)

(52) U.S. Cl.
CPC ...... *G01N 35/00009* (2013.01); *G01N 21/8483* (2013.01); *G01N 33/48764* (2013.01); *G01N 2035/00019* (2013.01)

(58) Field of Classification Search
CPC .................... G01N 21/8483; G01N 33/48764; G01N 35/00009; G01N 2035/00019
See application file for complete search history.

(56) References Cited

U.S. PATENT DOCUMENTS 8,226,793 B2    7/2012    Zimmer et al.
8,293,539 B2    10/2012   Petrich et al.
(Continued)

FOREIGN PATENT DOCUMENTS

EP    1424040 A1    6/2004
EP    1 593 434 A2    11/2005
(Continued)

OTHER PUBLICATIONS

International Search Report issued Jul. 6, 2013 in Application No. PCT/EP2012/068145, 4 pages.

*Primary Examiner* — Robert Clemente
(74) *Attorney, Agent, or Firm* — Woodard Emhardt Moriarty McNett and Henry LLP

(57) ABSTRACT

A test tape cassette is disclosed that includes a cassette housing and an analytical test tape. The test tape includes a plurality of analytical test elements, a spreading fabric for applying a body fluid, and an underlying reagent layer for detecting an analyte in the body fluid. The cassette housing has an application tip that has a guide path extending longitudinally to the test tape in an arched-shape and is uncurved at right angles thereto for supporting the test tape in a kink-free manner. The guide path has an apex area with a central opening that delimits a measuring window for an optical measurement on the test elements.

20 Claims, 6 Drawing Sheets

(56) References Cited

U.S. PATENT DOCUMENTS

| | | |
|---|---|---|
| 8,404,478 B2 | 3/2013 | Harttig et al. |
| 8,449,823 B2 | 5/2013 | Seelig et al. |
| 8,684,949 B2 | 4/2014 | Hoenes et al. |
| 2005/0201897 A1* | 9/2005 | Zimmer et al. ............ 422/82.05 |
| 2006/0173380 A1 | 8/2006 | Hoenes et al. |
| 2006/0216817 A1 | 9/2006 | Hoenes et al. |
| 2006/0240403 A1 | 10/2006 | List et al. |
| 2008/0049227 A1 | 2/2008 | Sacherer |
| 2011/0229960 A1 | 9/2011 | List et al. |
| 2011/0273715 A1 | 11/2011 | Seelig et al. |
| 2012/0045825 A1* | 2/2012 | Harttig et al. .............. 435/287.1 |
| 2013/0230428 A1 | 9/2013 | Seelig et al. |

FOREIGN PATENT DOCUMENTS

| | | |
|---|---|---|
| EP | 2011630 A1 * | 1/2009 |
| WO | WO 2005/006985 A2 | 1/2005 |

* cited by examiner

TEST TAPE CASSETTE AND ANALYTICAL TEST TAPE THEREFOR

CROSS-REFERENCE TO RELATED APPLICATIONS

This patent application is a continuation of Int'l Patent Application No. PCT/EP2012/068145; filed 14 Sep. 2012, which claims priority to and the benefit of EP Patent Application No. 11181718.5; filed 16 Sep. 2011. Each patent application is incorporated herein by reference as if set forth in its entirety.

TECHNICAL FIELD

This disclosure relates generally to engineering and medicine, and more particularly, it relates to analytical test tapes having grid-shaped spreading layers and test tape cassettes having an arch-shaped application tip that deflects the analytical test tape to provide test elements.

BACKGROUND

EP Patent Application Publication No. 1 878 379 describes a test tape cassette having a tape guide with a flat support frame on a measuring head that stretches test elements or test fields in a flat manner at the site of measurement. During a measurement, the test tape is bent, starting from deflecting bevels, over the sides of the frame that run perpendicular to the tape direction to achieve a freely stretched flat position. The label-like test elements or test fields used for the measurement have a central chemical carrier the side edges of which are engaged behind by a spreading fabric.

A possible disadvantage is that under the prevailing strains on the test tape structure on the flat support frame, a gap may form between the spreading net and a chemical carrier as illustrated here in FIG. 9. In FIG. 9, gap dimensions are largest in the center and decrease towards the sides, which can generate different capillary forces and ultimately result in undesired distributions (that may have a preferred direction) of the measuring medium.

It has been found that such a gap formation amplifies a tendency for "dewetting" (i.e., a migration of the blood sample from the wetted fabric meshes) and increases a sensitivity towards contaminants present on the skin of the user. The latter effect results from capillary blood collected by a skin puncture that forms a drop of blood at the puncture site in which contaminants are initially concentrated in the boundary area that is in contact with the skin. The "native" blood is then firstly distributed into the boundary areas of the chemical carrier due to the gap formation in the spreading fabric, while the contaminated blood that flows in afterwards then reaches the central measuring spot and can impair the measuring performance.

For the foregoing reasons, there is a need for optimized test tape cassettes, as well as disposable testing means used therein, that provide an improved reliability and accuracy of an analyte measurement.

BRIEF SUMMARY

In view of the disadvantages noted above, the disclosure describes analytical test tapes and test tape cassettes incorporating such test tapes that avoid or reduce gap formation between a spreading fabric and reagent layer. Briefly, disclosure is based upon an inventive concept that includes a spreading fabric with a modified bending stiffness and/or that includes a test tape guide geometry and test field structure in which gap formation between the spreading fabric and reagent layer is substantially minimized under operating conditions. The inventive concept therefore provides certain advantages, effects, features and objects when compared to known analytical test tapes and test tape cassettes and thereby minimizes gap formations that can impair measuring performance.

In one aspect, an analytical test tape is provided for use in a test tape cassette. The test tape includes a spreading fabric with a bending stiffness modified by at least one irregular change in a property of fabric threads in certain sections or locally. The at least one irregular change allows direction-dependent strains in an area of an application tip to be accordingly compensated for and taken into consideration thereby avoiding a gap formation. This can be optimized by adapting the bending stiffness of the spreading fabric to reduce gap formation between the spreading fabric and a reagent layer of a test field provided for the application of body fluid.

In some instances, the bending stiffness can be modified by a non-isotropic, area-by-area fabric modification. For example, fabric threads of the spreading fabric can be modified to have reduced thread cross-sections in places by, for example, laser ablation, etching or mechanical removal of material. Alternatively or additionally, the fabric threads can have a non-uniform design due to different thread materials, thread sizes, coatings or filament structures that modify the bending stiffness.

In other instances, the bending stiffness can be specifically adapted by locally varying the fabric geometry of the spreading fabric by, for example, detaching individual fabric threads.

With respect to the spreading fabric, it can be wider than the reagent layer and can be supported flat on the test tape by means of spacers in the area of its protruding side edges. This allows undesired gap formation associated with spreading fabric bending to be further suppressed.

To find a good compromise between an adequate minimum thickness for sample distribution and a radius of a wound-up, used test tape, the spreading fabric can have a thickness of less than 150 µm or alternatively less than 110 µm.

In another aspect, test tape cassette is provided having an application tip that has an arch-shaped guide path extending longitudinally to a test tape (or in the direction of tape travel). The application tip, however, is uncurved crosswise thereto for supporting the test tape in a kink-free manner, and that an apex area of the guide path delimits a central opening as a measuring window for an optical measurement on test elements. The arch-shaped longitudinal curvature of the guide path or running surface enables the bending stiffness of the test elements and in particular of the spreading fabric to be taken into account by means of an evenly supporting mechanical underbody, thus avoiding sharp tape bends and hence gap formation.

To avoid displacements in the multilayer structure, the tape curvature is only in one dimension, whereas an uncurved support is achieved in the tape transverse direction. At the same time, the arch-shaped guide path can ensure a targeted sample pick-up of even very small amounts of sample at the apex and, due to the measuring window positioned there in the form of a clear opening, also can enable a reduction of the required test field area.

In some instances, the arch-shaped guide path can have a fixed radius of curvature in a range from about 3 mm to about 5 mm and can have a longitudinal extension in a direction of tape transport in a range from about 5 mm to about 8 mm. In this manner, it is advantageous when the longitudinal extension of the guide path is the same or less than the length of the test elements, which can be in a range from about 5 mm to about 15 mm.

The operating conditions and in particular the tape pulling force should be adapted such that the test tape under tension is supported in a planar fashion on the guide path so that the spreading fabric lies essentially gap-free on the reagent layer.

To avoid gap formation under the unglued central area of the spreading fabric, it is advantageous when the reagent layer viewed in the tape transverse direction is narrower than the test tape and wider than the measuring window.

For an optimized optical detection of measured values from a rear side, it is advantageous when a housing wall of the application tip forming the guide path is beveled on the rear side towards the measuring window.

To achieve usage and manufacturing advantages, it is advantageous when the application tip is molded in one piece such as an injection molded part on the cassette housing and projects from the hand-held device in the operating state to punctually apply body fluid.

These and other advantages, effects, features and objects of the inventive concept will become better understood from the description that follows. In the description, reference is made to the accompanying drawings, which form a part hereof and in which there is shown by way of illustration, not limitation, embodiments of the inventive concept.

BRIEF DESCRIPTION OF THE DRAWINGS

The advantages, effects, features and objects other than those set forth above will become more readily apparent when consideration is given to the detailed description below. Such detailed description makes reference to the following drawings, wherein.

Figure 1:
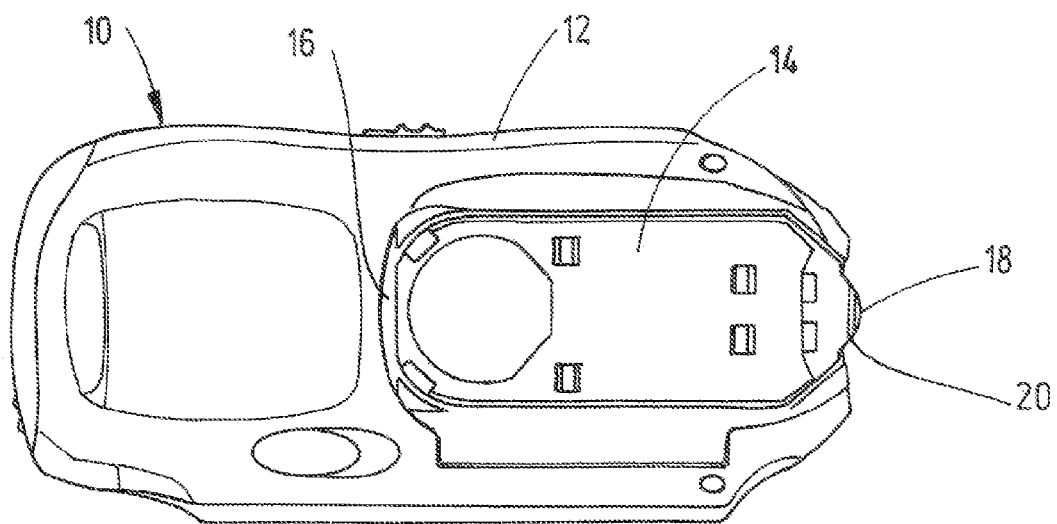
FIG. 1 shows a hand-held device for blood sugar tests that includes a test tape cassette inserted as a consumable in a partially broken side-view.

While the inventive concept is susceptible to various modifications and alternative forms, exemplary embodiments thereof are shown by way of example in the drawings and are herein described in detail. It should be understood, however, that the description of exemplary embodiments that follows is not intended to limit the inventive concept to the particular forms disclosed, but on the contrary, the intention is to cover all advantages, effects, features and objects falling within the spirit and scope thereof as defined by the embodiments described herein and the claims below. Reference should therefore be made to the embodiments described herein and claims below for interpreting the scope of the inventive concept. As such, it should be noted that the embodiments described herein may have advantages, effects, features and objects useful in solving other problems.

DESCRIPTION OF EXEMPLARY EMBODIMENTS

The analytical test tapes and test tape cassettes now will be described more fully hereinafter with reference to the accompanying drawings, in which some, but not all embodiments of the inventive concept are shown. Indeed, the test tapes and test tape cassettes may be embodied in many different forms and should not be construed as limited to the embodiments set forth herein; rather, these embodiments are provided so that this disclosure will satisfy applicable legal requirements.

Likewise, many modifications and other embodiments of the test tapes and test tape cassettes described herein will come to mind to one of skill in the art to which the disclosure pertains having the benefit of the teachings presented in the foregoing descriptions and the associated drawings. Therefore, it is to be understood that the test tapes and test tape cassettes are not to be limited to the specific embodiments disclosed and that modifications and other embodiments are intended to be included within the scope of the appended claims. Although specific terms are employed herein, they are used in a generic and descriptive sense only and not for purposes of limitation.

Unless defined otherwise, all technical and scientific terms used herein have the same meaning as commonly understood by one of skill in the art to which the disclosure pertains. Although any methods and materials similar to or equivalent to those described herein can be used in the practice or testing of the test tapes and test tape cassettes, the preferred methods and materials are described herein.

Moreover, reference to an element by the indefinite article "a" or "an" does not exclude the possibility that more than one element is present, unless the context clearly requires that there be one and only one element. The indefinite article "a" or "an" thus usually means "at least one." Likewise, the terms "have," "comprise" or "include" or any arbitrary grammatical variations thereof are used in a non-exclusive way. Thus, these terms may both refer to a situation in which, besides the feature introduced by these terms, no further features are present in the entity described in this context and to a situation in which one or more further features are present. For example, the expressions "A has B," "A comprises B" and "A includes B" may both refer to a situation in which, besides B, no other element is present in A (i.e., a situation in which A solely and exclusively consists of B) or to a situation in which, besides B, one or more further elements are present in A, such as element C, elements C and D, or even further elements.

Overview

Analytical test tapes having a carrier tape are provided for use in a test tape cassette. Such test tapes can be wound onto a spool and have a plurality of test elements that are distributed on the carrier tape in a tape longitudinal direction and have a spreading fabric for applying body fluid and an underlying reagent layer for detecting an analyte in the body fluid. In particular, the spreading fabric is formed from fabric threads that are crossed in a grid shape and with a bending stiffness modified by at least one irregular change in a property of fabric threads in certain sections or locally.

Test tape cassettes incorporating the analytical test tape also are disclosed. Such test tape cassettes can be inserted into a hand-held device and used, for example, in blood sugar tests. In particular, the test tape cassette housing has a test tape guide geometry and test field structure in such a manner that gap formation between the spreading fabric and chemical carrier/reagent layer is substantially minimized under operating conditions.

Analytical Test Tapes and Test Tape Cassettes

FIG. 1 shows an exemplary blood sugar measuring system 10. In particular, the system shown enables blood glucose determinations to be carried out locally on blood samples collected by a skin puncture. It is also possible to analyze other body fluids such as, for example, a tissue fluid.

The system includes a hand-held device 12 that can be held and used in the hand of a user as a mobile laboratory. To substantially simplify handling, a test tape cassette 14 can be inserted into a cassette slot 16 of the device 12 as an analytical consumable for storing a plurality of individual tests.

During an operating state (with the protective cap removed), an application tip 18 projects freely from the device 12 so that a test tape 20 can be deflected in this position to apply a drop of blood on the upper side to carry out a photometric analysis on the rear side.

Figure 2:
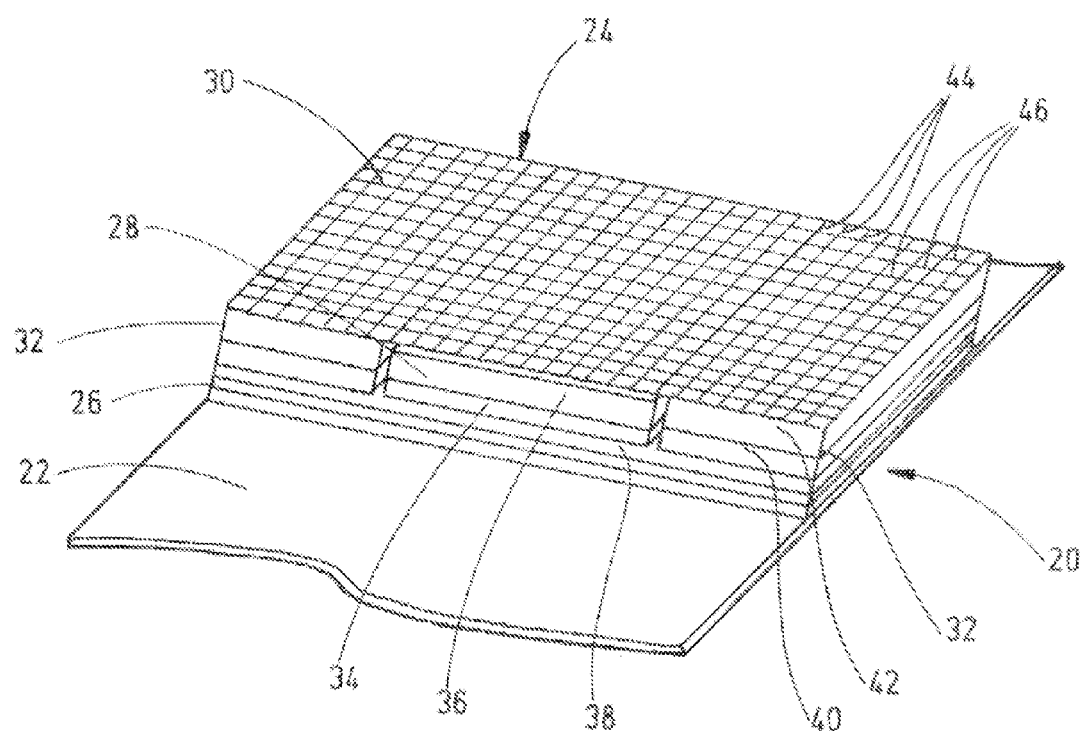
FIG. 2 shows a section of a test tape of the test tape cassette with an analytical test element in a perspective view.

FIG. 2 shows a section of the test tape 20 guided in the test tape cassette 14. The test tape 20 includes a windable, flexible transport tape 22 and a plurality of test elements 24 stored thereon for successive single use. The test elements 24 are spaced apart from one another in the tape longitudinal direction. In some instances, the transport tape 22 can be an about 5 mm wide and about 12 µm thick foil on which the test elements 24, each having a total height of about 200 µm, are mounted.

As used herein, "about" means within a statistically meaningful range of a value or values such as a stated concentration, depth, height, length, molecular weight, pH, sequence identity, time frame, temperature, volume or width. Such a value or range can be within an order of magnitude, typically within 20%, more typically within 10%, and even more typically within 5% of a given value or range. The allowable variation encompassed by "about" will depend upon the particular system under study, and can be readily appreciated by one of skill in the art.

The test elements 24 can be multilayered. In particular, the test elements 24 can be label-like flat structures with a rectangular outline having a double-sided adhesive strip 26 glued onto the transport tape 22, a chemical carrier 28 mounted thereon and a spreading fabric 30. The spreading fabric 30 spans the chemical carrier 28 on the upper side facing away from the transport tape 20 for a two-dimensional dispersion of a blood sample applied from above onto the spreading fabric. Spacers 32 are provided on the sides next to the chemical carrier 28 to support the whole area of the spreading fabric 30 in a flat and step-free manner.

The chemical carrier 28 includes a light-permeable carrier foil 34 and a reagent layer 36 mounted thereon, which is built up in a known manner from an upper pigment layer with an underlying dry chemistry film.

The spacers 32 include of a base strip 40 adhering to the upper adhesive layer 38 of the double-sided adhesive strip 26 and an adhesive layer 42 located thereon for laterally attaching the spreading fabric 30.

The spreading fabric 30, shown only schematically in FIG. 2 and with the thickness not to scale, can be formed by grid-like interlaced fabric threads 44, 46. As part of the inventive concept, it has been recognized the fabric threads can be connected together as warp threads 44 and weft threads 46 in plane weave and have a non-uniform structure to locally modify the bending stiffness as elucidated in more detail below. The spreading fabric 30, which has a thickness of about 100 µm, ensures a rapid uptake of the liquid sample onto the free upper side and a two-dimensional dispersion on the underlying reagent layer 36 due to its capillary interspaces.

The one-sided closure of the fabric openings by the adhesive material of the flanking adhesive layers 42 forms a type of honey comb structure above the spacers 32, which prevents blood flowing to the side edges of the test element 20. Thus, the liquid dispersion or spreading occurs in a targeted manner in the unglued central area of the spreading fabric 30 above the reagent layer 36, where it is possible to dispense with the hydrophobic edge strips of the prior art that are, for example, specifically applied as wax strips by means of thermal transfer printing, without disadvantages.

The dry chemistry film can be based on enzymes of the reagent layer 36 and responds to an analyte (e.g., glucose) by a color change so that a reflection-photometric detection can take place through the transparent foil composite 22, 26, 34 from the rear side of the test tape 20.

Figure 3:
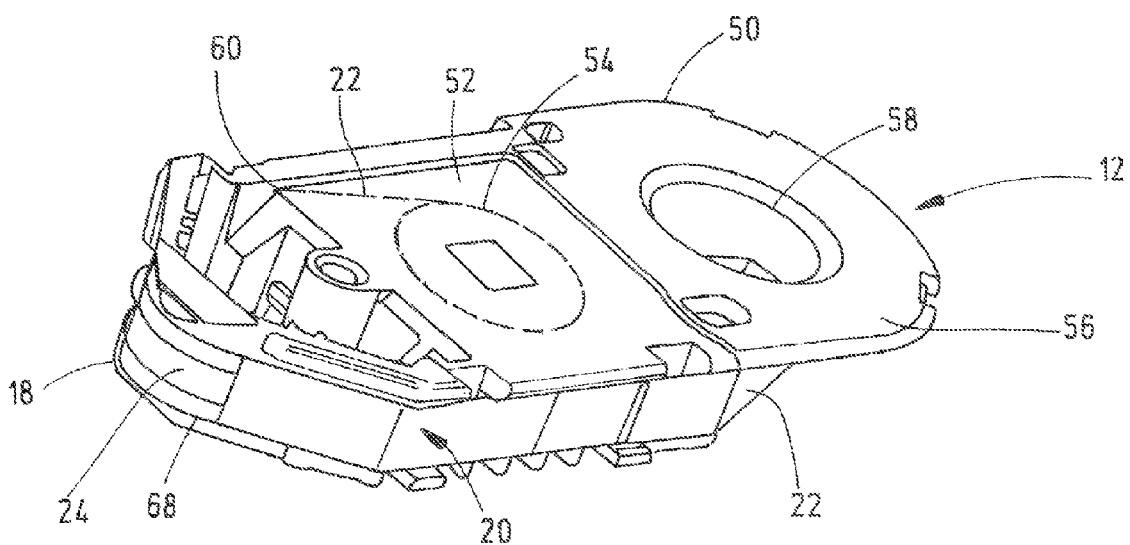
FIG. 3 shows a housing member of the test tape cassette in a perspective view.

FIG. 3 shows a cassette housing 50 of the test tape cassette 12 with the housing cover removed. The cassette housing 50 encloses a supply chamber 52 for a sealed storage of a supply spool 54 for unused test tape. A rotating driven take-up spool 58 for winding used test tape is mounted on a housing flange 56. Thus, the test tape 20 is pulled over a uniform tape guide formed by the cassette housing 50 from the supply spool 54, deflected over the application tip 18 and disposed of on the take-up spool 58, where a passage seal 60 on the supply chamber 52 ensures that tape tension is maintained.

In this manner, the test fields 24 can be successively brought into use on the application tip 18 by winding the transport tape 22 forward to apply a small amount of sample in a targeted manner. As a result of the pulling force exerted in this process, the multilayer tape structure is subjected to direction-dependent stretching or contractions especially in the area of narrow deflecting points.

Figure 9:
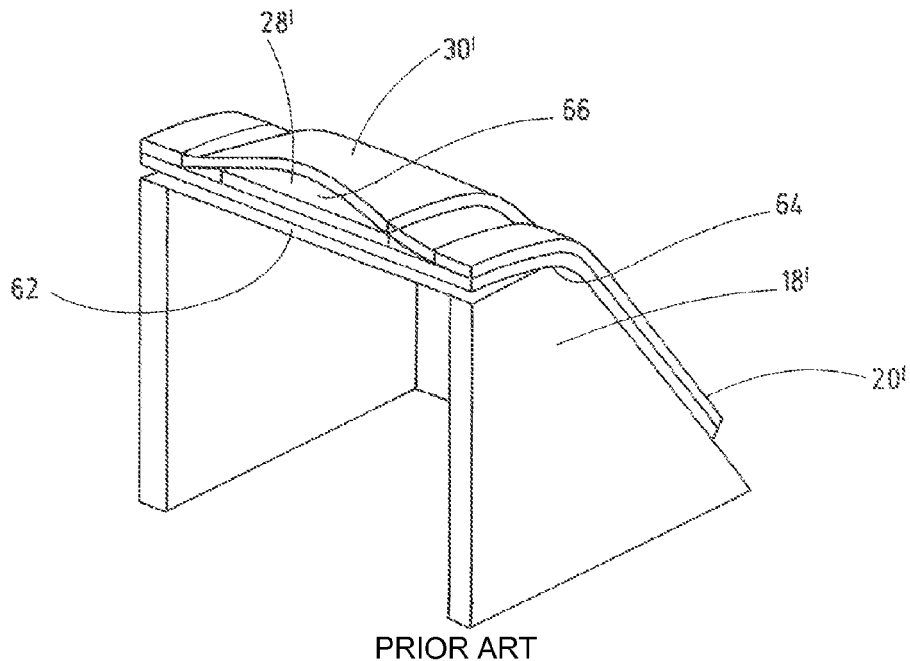
FIG. 9 shows a test field on an application tip according to the prior art in a cutaway perspective view.

In the case of the prior art as shown in FIG. 9 for a known application tip 18' with a flat support frame 62, the bending stiffness of the spreading fabric 30' in the longitudinal and transverse tape direction of test tape 20' can lead to a lifting or arching over the chemical carrier 28'. This effect is due, on the one hand, to bending at the narrow deflection points 64 and to tape arching in the transverse direction due to the lateral fabric bonding below the level of the chemical carrier 28'. This results in a gap formation 66 in the central area between the spreading fabric 30' and chemical carrier 28' that can impair sample transfer and thus the measurement result.

Figure 4:
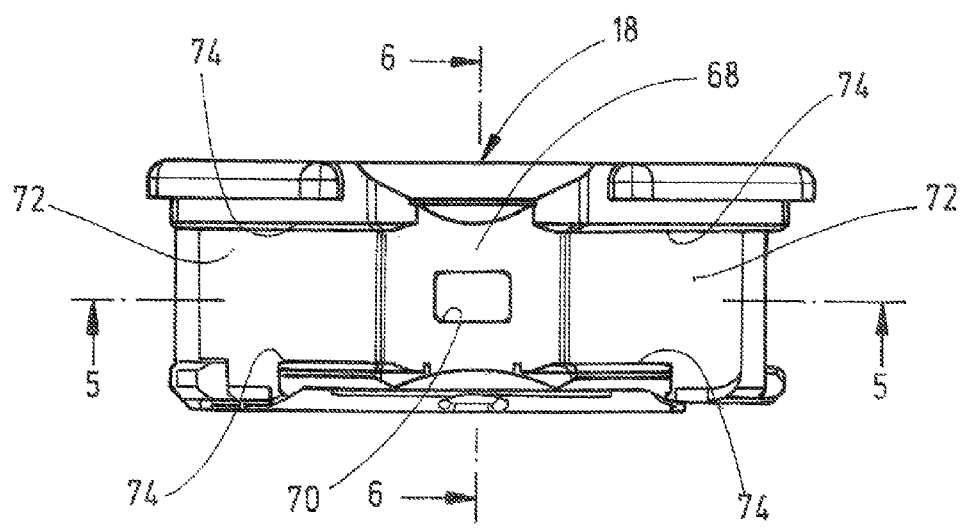
FIG. 4 shows an application tip of the test tape cassette in a top-view, in a longitudinal section and in cross-section.
Figure 5:
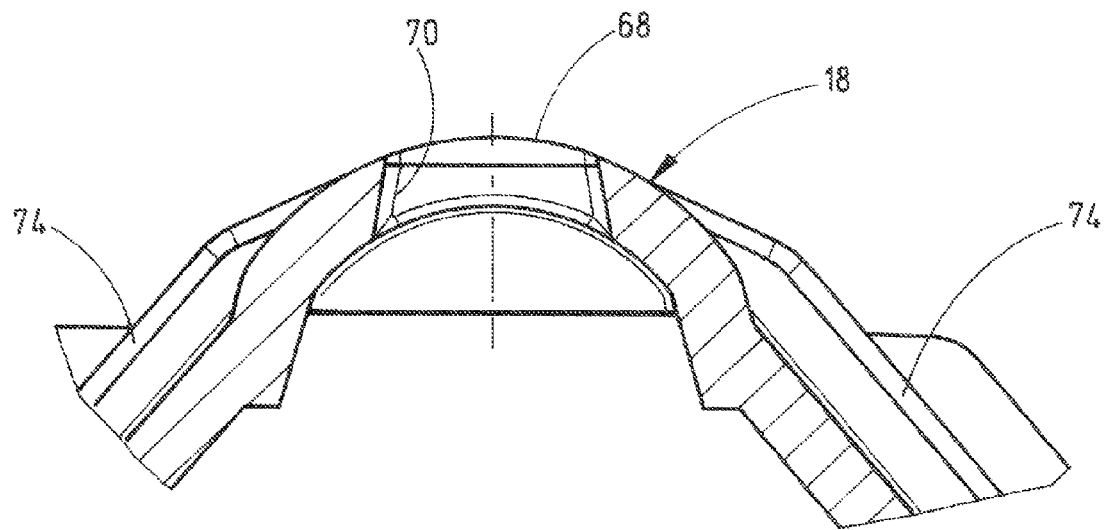
FIG. 5 and FIG. 6 show a section along the line 5-5 and 6-6 in FIG. 4, respectively.
Figure 6:
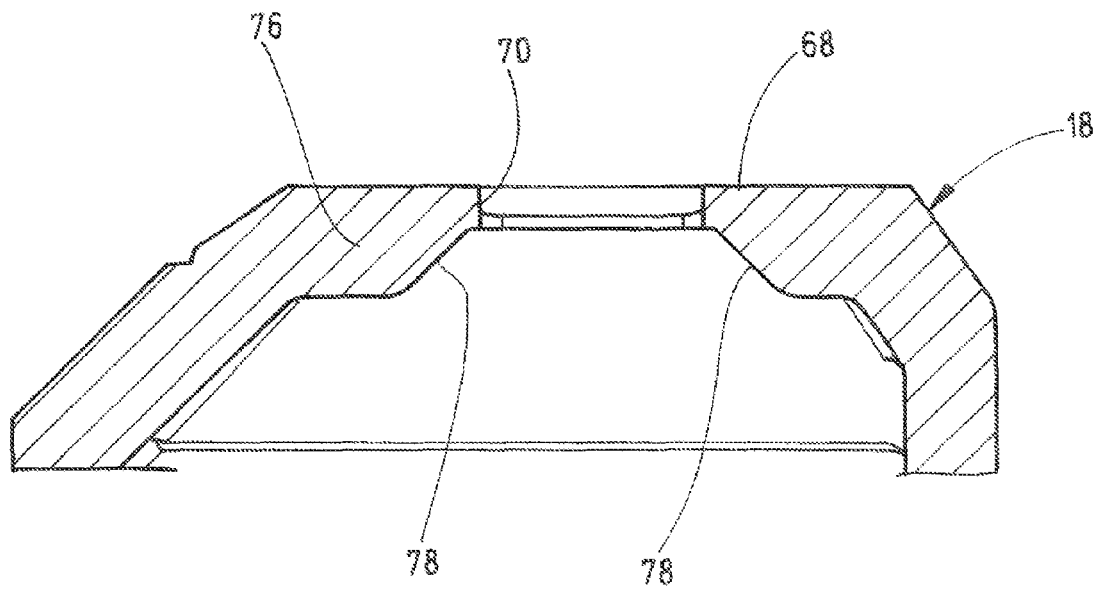

As part of the inventive concept, and to avoid the gap formation described above, the application tip 18 can be provided according to FIGS. 4-6 with an outwardly convex guide path 68 for the test tape 20 extending in an arched shape in the tape longitudinal direction or tape transport direction. The apex area of the guide path 68 delimits on all sides a central opening 70 as a measuring window for an optical measurement of the test elements 24 from the rear side.

To feed the test tape 20 into and away from the application tip 18, guide bevels 72, which enclose an acute angle, adjoin the ends of the guide path 68. Side boundaries 74 also can be provided in this area that secure the test tape 20 against lateral displacement while the guide path 68 remains free from such side boundaries.

As shown best in FIG. 5, the arch-shaped guide path 68 has a predetermined, defined radius of curvature in a range from about 3 mm to about 5 mm. Correspondingly, the guide path 68 can have a longitudinal extension in the tape transport direction in a range of about 5 mm to 8 about mm. In this manner, it is expedient when the test elements 24 are adapted to the longitudinal extension of the guide path 68. It is particularly advantageous to shorten the test elements 24 to a length that is as short as possible to avoid tensile and shearing stresses caused by deflecting points.

As shown best in FIG. 6, the arch-shaped guide path 68 is uncurved or linear when viewed in the tape transverse direction so that the spreading fabric 30 is only bent in one dimension in the tape longitudinal direction and in doing so lies essentially gap-free on the reagent layer 36. The reagent layer 36 is advantageously wider than the measuring window 70 so that the measuring spot in every case lies on the reagent layer 36. The housing wall 76 of the application tip 18 formed on the front side as the guide path 68 is beveled on its rear side 78 towards the measuring window 70 for the beam path of the photometric measuring optics.

The bending stiffness of the spreading fabric 30 is appropriately modified in some areas or locally as a further measure for avoiding or reducing gap formation between the spreading fabric 30 and the reagent layer 36.

In general, the bending stiffness of a fabric sample can be determined by the cantilever method. In this method, the bending behavior under its own weight is determined by measuring a bending length at which the fabric sample is bent downwards under its own weight by a defined angle. For example, a high bending stiffness in the tape transverse direction can be provided to ensure a required flatness of the spreading fabric. However, a low bending stiffness in the tape longitudinal direction also may be necessary to be able to deflect the spreading fabric without undesired arching or a delamination of other parts of the overall test element structure occurring.

An isotropic fabric with uniform weft and warp threads can, depending on the thread thickness and fabric thickness, only have one uniformly high or low bending stiffness in relation to the desired test element architecture.

To obtain a sufficiently thick spreading fabric for the test function with areas of high bending stiffness and at the same time with areas of low bending stiffness, there are the following methods of modifying the bending stiffness in certain areas or locally:

- using threads of different thicknesses in appropriate areas of the fabric;
- detaching individual threads in certain areas;
- adding an additional coating in certain areas;
- diluting or local weakening of one or more threads;
- using different thread materials; and
- using different thread qualities (e.g., multifilament threads).

Figure 7:
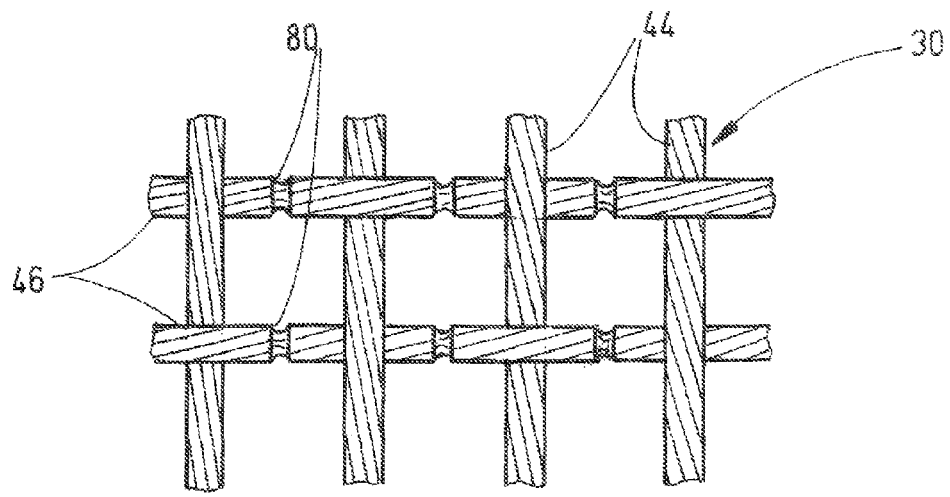
FIG. 7 shows a spreading fabric for an analytical test element with weakened spots in a partial top-view.

FIG. 7 shows an exemplary spreading fabric 30 in which only one of the thread systems 44, 46 (e.g., the weft threads 46) has reduced thread cross-sections at certain positions. This can be generated by providing the fabric threads 46 in the prefabricated spreading fabric 30 with weakened spots 80 by means of laser ablation. Alternatively, the weakened spots 80 can be generated by etching methods or by mechanical removal of material, for example, by means of a wafer saw. Regardless of the method used, the introduced, local weakened spots reduce the bending stiffness of the spreading fabric 30.

Figure 8:
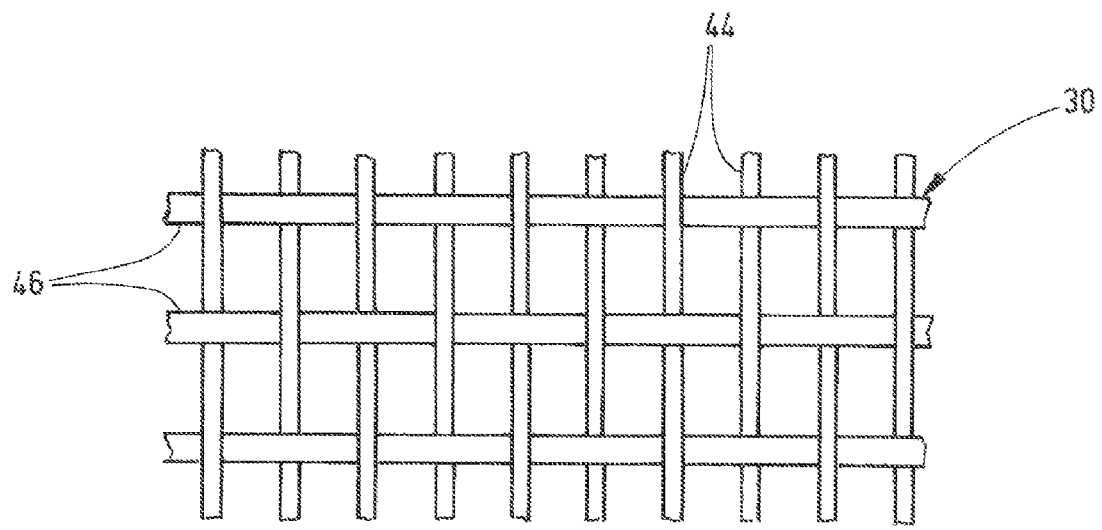
FIG. 8 shows a further embodiment of a modified spreading fabric.

FIG. 8 shows another exemplary spreading fabric 30 in which the bending stiffness is modified by different thread thicknesses in the area of its two thread systems. Here, the warp threads 44 have a lower thread thickness and consequently a lower bending stiffness than the thicker weft threads 46. It also would be possible to locally vary the fabric geometry of the spreading fabric 30 by, for example, detaching individual fabric threads.

All of the patents, patent applications, patent application publications and other publications recited herein are hereby incorporated by reference as if set forth in their entirety.

The present inventive concept has been described in connection with what are presently considered to be the most practical and preferred embodiments. However, the inventive concept has been presented by way of illustration and is not intended to be limited to the disclosed embodiments. Accordingly, one of skill in the art will realize that the inventive concept is intended to encompass all modifications and alternative arrangements within the spirit and scope of the inventive concept as set forth in the appended claims.

The invention claimed is:

1. A test tape cassette for insertion into a hand-held device, the cassette comprising:
   a cassette housing for storing at least two tape spools; and
   an analytical test tape that can be wound forwards by means of the at least two tape spools, wherein the analytical test tape comprises a plurality of analytical test elements stored thereupon having a spreading fabric and an underlying reagent layer for detecting an analyte of interest,
   wherein the cassette housing has an application tip that deflects the analytical test tape to provide at least one of the plurality of test elements, the application tip having a guide path that extends in an arch shape longitudinally to the analytical test tape and is uncurved at right angles thereto for supporting the analytical test tape in a kink-free manner, wherein an apex area of the guide path delimits a central opening as a measuring window for an optical measurement on the at least one of the plurality of test elements,
   wherein the test tape when under tension is supported in a planar fashion on the guide path so that the spreading fabric lies gap-free on the underlying reagent layer, and
   wherein the application tip comprises a housing wall that is beveled on a rear side towards the measuring window.

2. The test tape cassette of claim 1, wherein the arch-shaped guide path has a fixed radius of curvature in a range from 3 mm to about 5 mm.

3. The test tape cassette of claim 1, wherein the guide path has a longitudinal extension in a direction of tape transport in a range from about 5 mm to about 8 mm.

4. The test tape cassette of claim 1, wherein the guide path has a longitudinal extension in a direction of tape transport that is the same or less than a length of the test elements and is in a range from about 5 mm to about 15 mm.

5. The test tape cassette of claim 1, wherein the reagent layer, when viewed in a tape transverse direction, is narrower than the analytical test tape and wider than the measuring window.

6. The test tape cassette of claim 1, wherein the application tip comprises a housing wall that is beveled on a rear side towards the measuring window.

7. The test tape cassette of claim 1, wherein the application tip is a molded part on the cassette housing and projects from the hand-held device in an operating state to punctually apply a sample fluid.

8. The test cassette of claim 1, wherein:
   the tape has a longitudinal direction and a transverse direction that is transverse to the longitudinal direction; and
   the spreading fabric in the longitudinal direction has a bending stiffness that is lower than in the transverse direction.

9. The test cassette of claim 8, wherein the spreading fabric has one of the thread systems with weakened spots.

10. The test cassette of claim 9, wherein:
the thread systems include warp threads and weft threads; and
the weft threads have the weakened spots.

11. The test cassette of claim 8, wherein the spreading fabric has one of the thread systems with thread thicknesses different from the others.

12. The test cassette of claim 11, wherein:
the thread systems include warp threads and weft threads; and
the warp threads have a lower thread thickness than the weft threads.

13. The test cassette of claim 8, wherein the bending stiffness is a measure of length of the spreading fabric at which the spreading fabric is bent at a defined angle under the weight of the spreading fabric.

14. A test tape cassette for insertion into a hand-held device, the cassette comprising:
a cassette housing for storing at least two tape spools; and
an analytical test tape that can be wound forwards by means of the at least two tape spools, wherein the analytical test tape comprises a plurality of analytical test elements stored thereupon having a spreading fabric and an underlying reagent layer for detecting an analyte of interest,
wherein the cassette housing has an application tip that deflects the analytical test tape to provide at least one of the plurality of test elements, the application tip having a guide path that extends in an arch shape longitudinally to the analytical test tape and is uncurved at right angles thereto for supporting the analytical test tape in a kink-free manner, wherein an apex area of the guide path delimits a central opening as a measuring window for an optical measurement on the at least one of the plurality of test elements,
wherein the test tape when under tension is supported in a planar fashion on the guide path so that the spreading fabric lies gap-free on the underlying reagent layer, and
wherein the reagent layer, when viewed in a tape transverse direction, is narrower than the analytical test tape and wider than the measuring window.

15. A test tape cassette, comprising:
an analytical test tape having a longitudinal direction and a transverse direction that is transverse to the longitudinal direction, wherein the test tape includes
a transport tape, and
a plurality of analytical test elements stored on the transport tape, wherein the test elements are spaced apart from one another in the longitudinal direction of the test tape, wherein the test elements each include
a reagent layer to detect analyte, and
a spreading fabric covering the reagent layer;
an application tip having a guide path around which the test tape is bent, wherein the guide path is convex relative to the test tape in the longitudinal direction and flat in the transverse direction; and
wherein the spreading fabric in the longitudinal direction has a bending stiffness that is lower than in the transverse direction.

16. The test cassette of claim 15, wherein the spreading fabric has a thread system with weakened spots.

17. The test cassette of claim 16, wherein:
the thread system includes warp threads and weft threads; and
the weft threads have the weakened spots.

18. The test cassette of claim 15, wherein the spreading fabric has a thread system with thread thicknesses different from the others.

19. The test cassette of claim 18, wherein:
the thread system includes warp threads and weft threads; and
the warp threads have a lower thread thickness than the weft threads.

20. The test cassette of claim 15, wherein the bending stiffness is a measure of length of the spreading fabric at which the spreading fabric is bent at a defined angle under the weight of the spreading fabric.

* * * * *